United States Patent
Kaneko et al.

(10) Patent No.: US 6,809,080 B2
(45) Date of Patent: Oct. 26, 2004

(54) MACROLIDE ANTIBIOTICS

(75) Inventors: Takushi Kaneko, Guilford, CT (US); William Thomas McMillen, Indianapolis, IN (US)

(73) Assignee: Pfizer, Inc., New York, NY (US)

(*) Notice: Subject to any disclaimer, the term of this patent is extended or adjusted under 35 U.S.C. 154(b) by 0 days.

(21) Appl. No.: 09/892,081

(22) Filed: Jun. 26, 2001

(65) Prior Publication Data

US 2002/0052328 A1 May 2, 2002

Related U.S. Application Data

(60) Provisional application No. 60/215,237, filed on Jun. 30, 2000.

(51) Int. Cl.$^7$ .......................... A61K 31/70; C07H 17/08
(52) U.S. Cl. ......................................... 514/29; 536/7.4
(58) Field of Search .................. 514/29; 536/7.4, 536/7.2, 7.3

(56) References Cited

U.S. PATENT DOCUMENTS

| 5,747,467 | A | 5/1998 | Agouridas et al. ............ 514/29 |
| 6,121,432 | A | 9/2000 | Bonnet et al. ................ 536/7.2 |
| 6,124,269 | A | 9/2000 | Phan et al. .................... 514/29 |
| 6,313,101 | B1 | 11/2001 | Denis et al. ................... 514/29 |
| 6,352,983 | B1 | 3/2002 | Agouridas et al. ........... 514/220 |
| 6,355,620 | B1 * | 3/2002 | Ma et al. ....................... 514/29 |
| 6,440,941 | B1 | 8/2002 | Denis ........................... 514/29 |
| 6,455,505 | B2 | 9/2002 | Agouridas et al. ............ 514/29 |
| 6,569,836 | B2 | 5/2003 | Phan et al. .................... 514/29 |
| 6,590,083 | B1 | 7/2003 | Hlasta et al. ................. 536/7.4 |

FOREIGN PATENT DOCUMENTS

| EP | 1114826 | 7/2001 | ........... C07H/17/08 |
| WO | WO0140241 | 6/1971 | ........... C07H/17/00 |
| WO | WO9921871 | 5/1999 | ........... C07H/17/08 |
| WO | WO0026224 | 5/2000 | ........... C07H/17/00 |
| WO | WO0044761 | 8/2000 | ........... C07H/17/00 |
| WO | WO0063224 | 10/2000 | ........... C07H/17/06 |
| WO | WO0071557 | 11/2000 | ........... C07H/17/08 |

OTHER PUBLICATIONS

USSN 10/441,347; Yong–Jin Wu, et al., filed on May 19, 2003.

* cited by examiner

*Primary Examiner*—Elli Peselev
(74) *Attorney, Agent, or Firm*—Peter C. Richardson; Gregg C. Benson; Frank W. Forman

(57) ABSTRACT

This invention relates to compounds of the formula

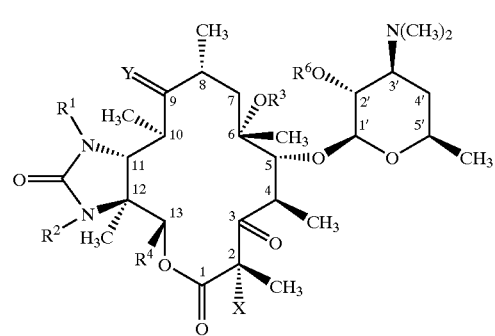

and to pharmaceutically acceptable salts, prodrugs, and solvates thereof wherein X, Y, $R^1$, $R^2$, $R^3$, $R^4$, and $R^6$ are as defined herein. The compounds of formula I are antibacterial and antiprotozoal agents that may be used to treat various bacterial and protozoal infections and disorders related to such infections. The invention also relates to pharmaceutical compositions containing the compounds of formula I, methods of making the compounds, and to methods of treating bacterial and protozoal infections by administering the compounds.

9 Claims, No Drawings

MACROLIDE ANTIBIOTICS

This application claims priority of Ser. No. 60/215,237, filed Jun. 30, 2000, the text of which application is hereby incorporated by reference herein.

BACKGROUND OF THE INVENTION

This invention relates to macrolide compounds that are useful as antibacterial and antiprotozoal agents in mammals, including man, as well as in fish and birds. This invention also relates to methods of preparing the compounds, intermediates useful in preparation of the compounds, and pharmaceutical compositions containing the compounds. In addition, the present invention includes methods of treating bacterial and protozoal infections through the administration of the compounds to mammals, fish and birds requiring such treatment.

Derivatives of erythromycin A that are useful as antibiotic agents are referred to in International patent applications WO 98/56800, published Dec. 17, 1998; WO 98/51696, published Nov. 19, 1998; WO 99/21866, published May 6, 1999; WO 99/62920, published Dec. 9, 1999; WO 99/21865, published May 6, 1999; PCT/IB99/01701, filed Oct. 18, 1999; European patent application EP 895999, published Feb. 10, 1999; U.S. patent application Ser. No. 60/117,342, filed Jan. 27, 1999; U.S. patent application Ser. No. 60/130,809, filed Apr. 23, 1999; U.S. patent application Ser. No. 60/130,912, filed Apr. 23, 1999; and U.S. patent application Ser. No. 60/130,913, filed Apr. 23, 1999. Derivatives of erythromycin A are also referred to in U.S. Pat. Nos. 4,474,768 and 4,517,359, relating to the commercially available antibiotic azithromycin. These patents and patent applications are incorporated by reference herein in their entireties.

SUMMARY OF THE INVENTION

The present invention relates to compounds of the formula

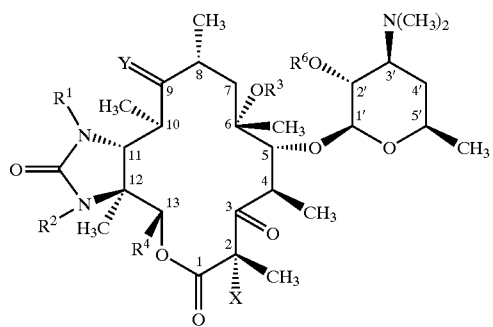

I and to pharmaceutically acceptable salts, prodrugs and solvates thereof, wherein:

X is C, Br, I, or F;

Y is =O, or =NOR$^5$ or Y means both —H and —OR$^5$; or both —H and —NR$^5$R$^{10}$ (i.e. Y is double bonded to the macrolide ring where it is =O or =NOR$^5$, or refers to two single bonded groups where it is both —H and —OR$^5$; or both —H and —NR$^5$R$^{10}$);

R$^1$, R$^2$, and R$^3$ are independently selected from H, C$_1$–C$_{10}$ alkyl, C$_2$–C$_{10}$ alkenyl, C$_2$–C$_{10}$ alkynyl, (4- to 10-membered heterocyclic) C$_1$–C$_6$ alkyl, (4- to 10-membered heterocyclic) C$_2$–C$_6$ alkenyl, (4- to 10-membered heterocyclic) C$_2$–C$_6$ alkynyl, (C$_6$–C$_{10}$ aryl) C$_1$–C$_6$ alkyl, (C$_6$–C$_{10}$ aryl) C$_2$–C$_6$ alkenyl, and (C$_6$–C$_{10}$ aryl) C$_2$–C$_6$ alkynyl wherein said alkyl moieties of the foregoing groups are optionally substituted by halo or C$_1$–C$_6$ alkyl, and wherein said heterocyclic moieties are optionally substituted by 4- to 10-membered heterocyclic, (4- to 10-membered heterocyclic) C$_1$–C$_6$ alkyl, or (C$_6$–C$_{10}$ aryl) C$_1$–C$_6$ alkyl, and further wherein the aryl and heterocyclic moieties of each of the foregoing groups and optional substituents is optionally substituted by 1 to 4 R$^7$ groups;

R$^4$ is selected from H, C$_1$–C$_{10}$ alkyl, C$_2$–C$_6$ alkenyl, C$_2$–C$_6$ alkynyl, (C$_1$–C$_6$ alkoxy) C$_1$–C$_6$ alkyl, (C$_1$–C$_6$ alkylthio) C$_1$–C$_6$ alkyl, (C$_5$–C$_8$ cycloalkyl) C$_2$–C$_5$ alpha branched alkyl, C$_3$–C$_8$ cycloalkyl, C$_5$–C$_8$ cycloalkenyl, 3 to 6 membered O or S containing heterocyclic group, or phenyl, wherein each R$^4$ group may be substituted with from 1 to 3 substituents independently selected from hydroxy, halo, (C$_6$–C$_{10}$ aryl) C$_2$–C$_6$ alkenyl, and C$_1$–C$_4$ alkyl;

R$^5$ and R$^{10}$ are independently selected from H, C$_1$–C$_6$ alkyl, C$_6$–C$_{10}$ aryl, 4- to 10-membered heterocyclic, (4- to 10-membered heterocyclic) C$_1$–C$_6$ alkyl and (C$_6$–C$_{10}$ aryl) C$_1$–C$_6$ alkyl, wherein said aryl and heterocyclic groups are optionally substituted by 1 to 4 R$^7$ groups;

R$^6$ is H, —C(O)C$_1$–C$_6$ alkyl, benzyl, benzyloxycarbonyl, or (C$_1$–C$_6$ alkyl)$_3$ silyl;

R$^7$ is independently selected from halo, cyano, nitro, trifluoromethyl, trifluoromethoxy, azido, —C(O)R$^8$, —C(O)OR$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_2$–C$_5$ alkenyl, C$_2$–C$_6$ alkynyl, C$_6$–C$_{10}$ aryl, 4- to 10-membered heterocyclic, and C$_1$–C$_6$ alkoxy; and each R$^8$ and R$^9$ is independently selected from H, C$_1$–C$_6$ alkyl, C$_6$–C$_{10}$ aryl, and 4- to 10-membered heterocyclic.

In one embodiment of the invention, Y is =O or =NOR$^5$, R$^1$ is (4- to 10-membered heterocyclic) C$_1$–C$_6$ alkyl substituted by 4- to 10-membered heterocyclic, R$^2$ is C$_1$–C$_{10}$ alkyl or C$_2$–C$_{10}$ alkenyl, R$^3$ is C$_1$–C$_6$ alkyl, R$^4$ is ethyl, R$^5$ is C$_1$–C$_6$ alkyl, and R$^6$ is H.

In another embodiment, the compound of the invention has the following formula:

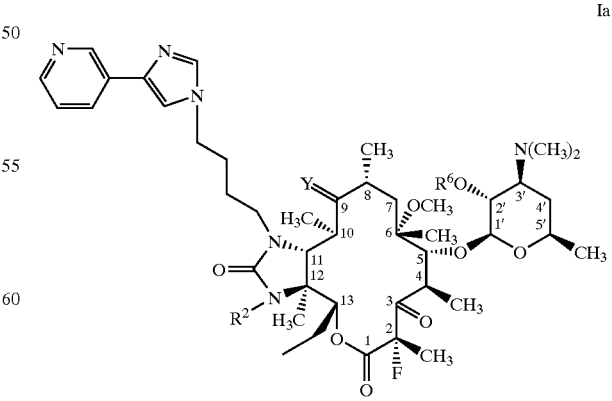

Ia

In one embodiment of the compound of formula Ia, Y is =O or =NOR$^5$, R$^2$ is C$_1$–C$_{10}$ alkyl or C$_2$–C$_{10}$ alkenyl, and R⁶ is H, —C(O)C₁–C₆ alkyl, benzyl, benzyloxycarbonyl, or (C₁–C₆ alkyl)₃ silyl. In one aspect of this embodiment, Y is =O and R⁶ is H. In another aspect of this embodiment, Y is =NOR⁵ and R⁶ is H. Preferably, in this embodiment, R² is CH₃, CH₂CH₃, CH₂CH=CH₂, trans-CH₂CH=CHCH₃, trans-CH₂CH=CHCH₂CH₃, or trans-CH₂—CH=C(CH₃)CH₂CH₂CH=(CH₃)CH₃.

The invention also relates to a pharmaceutical composition for the treatment of a bacterial infection or a protozoa infection in a mammal, fish, or bird which comprises a therapeutically effective amount of a compound of formula I, or a pharmaceutically acceptable salt, prodrug, or solvate thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula I or a pharmaceutically acceptable salt, prodrug, or solvate thereof.

The term "treatment", as used herein, unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or Peptostreptococcus spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionelia pneumophila, Streptococcus pneumoniae, Haemophilus influenzae,* or *Chiamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), vindans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobactedium avium* complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordeteila pertussis;* gas gangrene related to infection by *Clostridium perfringens* or Bacteroides spp.; and atherosclerosis related to infection by *Helicobacter pylon* or *Chlamydia pneumoniae.* Bacterial infections and protozoa infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobacterium necrophorum* or *Bacteroides nodosus;* cow pink-eye related to infection by *Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius,* coagulase neg. Staph. or *P. multocida;* and dental or mouth infections in dogs and cats related to infection by *Alcaligenes spp., Bacteroides spp., Clostridium spp., Enterobacter spp., Eubacterium, Peptostreptococcus, Porphyromonas,* or *Prevotella.* Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a method of preparing the above compound of formula I, or a pharmaceutically acceptable salt thereof, which comprises deprotecting a compound of the formula

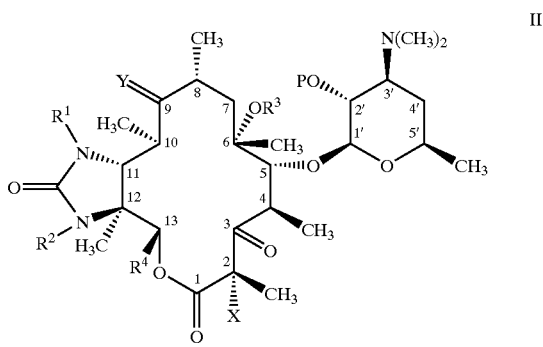

wherein P is a protecting group.

In a further aspect of the above process of preparing the compound of formula I, or a pharmaceutically acceptable salt thereof, the above compound of formula II is prepared by treating a compound of the formula

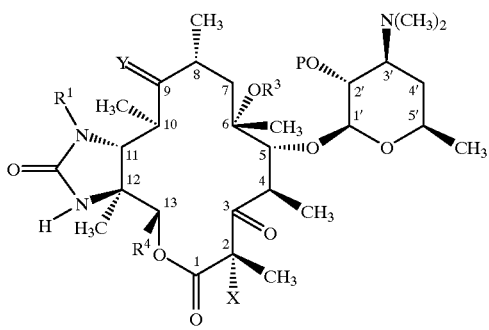

with a strong base and a compound of formula R²-L, where L is a leaving group.

The term "Me", as used herein, unless otherwise indicated, refers to methyl.

The term "Et", as used herein, unless otherwise indicated, refers to ethyl.

The term "Pr", as used herein, unless otherwise indicated, refers to propyl.

The term "Ac", as used herein, unless otherwise indicated, refers to acetyl.

The term "hydroxy protecting group", as used herein, unless otherwise indicated, includes acetyl, benzyloxycarbonyl, and various hydroxy protecting groups familiar to those skilled in the art including the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo.

The term "alkyl", as used herein, unless otherwise indicated, includes saturated monovalent hydrocarbon radicals having straight, cyclic or branched moieties, or mixtures thereof. It is to be understood that where cyclic moieties are intended, at least three carbons in said alkyl must be present. Such cyclic moieties include cyclopropyl, cyclobutyl and cyclopentyl.

The term "alkenyl", as used herein, unless otherwise indicated, includes straight-chain or branched-chain mono- or poly-unsaturated aliphatic hydrocarbon radicals containing at least one carbon-carbon double bond. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl", as used herein, unless otherwise indicated, includes straight-chain or branched-chain mono- or poly-unsaturated aliphatic hydrocarbon radicals containing at least one carbon-carbon triple bond. Examples of alkynyl radicals include, but are not limited to, ethynyl, propynyl, isopropynyl, butynyl, isobutynyl, pentynyl, hexynyl and the like.

The term "alkoxy", as used herein, unless otherwise indicated, includes — alkyl groups wherein alkyl is as defined above.

The term "aryl", as used herein, unless otherwise indicated, includes an organic radical derived from an aromatic hydrocarbon by the removal of one hydrogen. Examples of aryl radicals include, but are not limited to, phenyl, naphthyl, indenyl, indanyl, azulenyl, fluorenyl, anthracenyl and the like.

The term "4- to 10-membered heterocyclic", as used herein, unless otherwise indicated, includes aromatic and non-aromatic heterocyclic groups containing one or more heteroatoms, each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxygen or nitrogen atoms. The heterocyclic groups also include partially unsaturated or fully saturated 4- to 10-membered ring systems, e.g., single rings of 4 to 8 atoms in size and bi- or tricyclic ring systems, including aromatic 6-membered aryl or heteroaryl rings fused to a non-aromatic ring. An example of a 4-membered heterocyclic group is azetidinyl (derived from azetidine). An example of a 5-membered heterocyclic group is thiazolyl, and an example of a 10-membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "protecting group" refers to a suitable chemical group that may be attached to a functional group and removed at a later stage to reveal the intact functional group. Examples of suitable protecting groups for various functional groups are described in T. W. Greene and P. G. M Wuts, *Protective Groups in Organic Synthesis,* 2d *Ed.*, John Wiley and Sons (1991); L. Fieser and M. Fieser, *Fieser and Fieser's Reagents for Organic Synthesis,* John Wiley and Sons (1994); and L. Paquette, ed. *Encyclopedia of Reagents for Organic Synthesis,* John Wiley and Sons (1995).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

The compounds of this invention, including the compounds of formula I, include pharmaceutically acceptable derivatives or prodrugs thereof. A "pharmaceutically acceptable derivative or prodrug" means any pharmaceutically acceptable salt, ester, salt of an ester or other derivative of a compound of this invention that, upon administration to a recipient, is capable of providing (directly or indirectly) a compound of this invention or a metabolite or residue thereof. Particularly favored derivatives and prodrugs are those that increase the bioavailability of the compounds of this invention when such compounds are administered to a patient (e.g., by allowing an orally administered compound to be more readily absorbed into the blood), enhance delivery of the parent compound to a given biological compartment, increase solubility to allow administration by injection, alter metabolism or alter rate of excretion.

Compounds of formula I can be converted into prodrugs through, for example, free amino, amido, hydroxy or carboxylic groups. Examples of such prodrugs include compounds wherein an amino acid residue, or a polypeptide chain of two or more (e.g., two, three or four) amino acid residues is covalently joined through an amide or ester bond to a free amino, hydroxy or carboxylic acid group of a compound of formula I. The amino acid residues include but are not limited to the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates and phosphoryloxymethyloxycarbonyls, as outlined in D. Fleisher et al., *Advanced Drug Delivery Reviews*, vol. 19, p. 115 (1996). Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Medicinal Chemistry*, vol. 39, p. 10 (1996).

The compounds of this invention also include pharmaceutically acceptable salts of the compounds of formula I. The term "pharmaceutically acceptable salt(s)", as used herein, unless otherwise indicated, includes salts of acidic or basic groups that may be present in the compounds of the present invention.

Compounds of the invention may exist in tautomeric form. All tautomers of the compounds of formula I are included in the invention.

DETAILED DESCRIPTION OF THE INVENTION

All patents, publications, and patent applications referred to herein are hereby incorporated by reference in their entireties.

The compounds of the present invention may be prepared according to Scheme 1. In the Scheme, unless otherwise indicated, all of the substituents are as defined above.

The starting materials used in the present invention may require proper functional group protection before various modifications can take place, and deprotection after desired modifications are complete. Hydroxyl groups are generally protected as acetates or Cbz carbonates. The relative reactivity of various hydroxyl groups in the macrolide molecules of the general type claimed in this invention has been well established. Such differences in reactivity permit selective modification of different parts of the compounds of this invention.

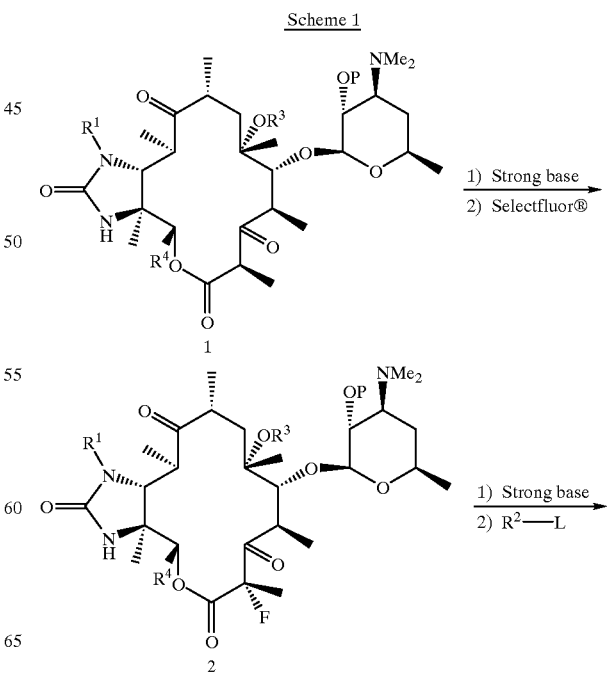

Scheme 1

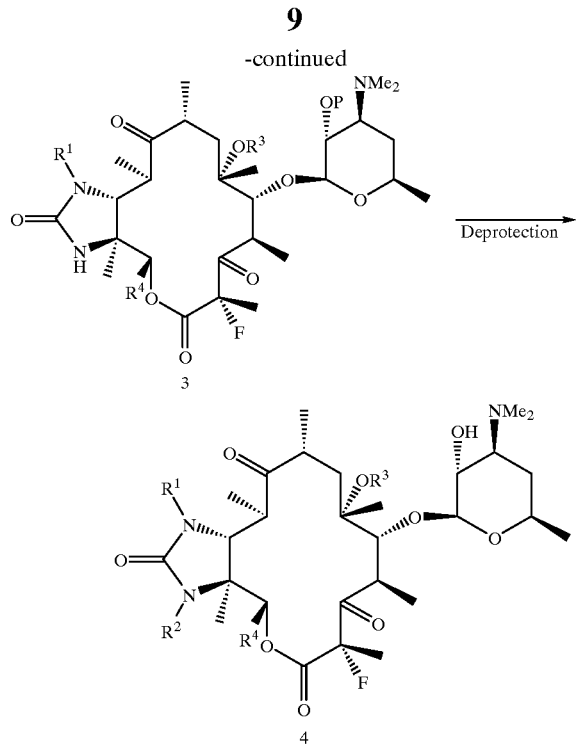

Cyclic urea 1 can be prepared according to PCT/IB99/01701, filed Oct. 18, 1999. Compound 1 ($R^1$=H) is then treated with a strong base such as potassium hexamethyldisilazide (KHMDS), lithium diisopropylamide (LDA), or sodium hydride in an inert solvent such as DMF or THF at a temperature of −78° to 0° C., preferably −78° C., for 5 minutes to 3 hours, preferably 15 minutes.

A fluorinating agent such as Selectfluor™ or N-fluorosuccinimide is then added. The solution is stirred at a temperature of −78° to 0°, preferably −78°, for 5 minutes to 5 hours, preferably 10 minutes, to give 2. The reaction mixture is then treated with another equivalent of a strong base, preferably KHMDS, t a temperature of −78° to 0°, preferably −78°, for 5 minutes to 3 hours, preferably 15 minutes, and one or slightly more than one equivalent of $R^2$-L is added, where I is a leaving group such as halogen, mesylate or tosylate. The solution is stirred at a temperature −78° to 0°, preferably −78°, for 5 minutes to 3 hours, preferably 15 minutes. The product 3 is isolated by extraction.

The protecting group P is then conventionally removed. For example, where P is Ac, this is done by stirring in wet methanol at 0° C. to 50° C., preferably room temperature, for 0.5 hr to 20 hours, preferably 12 hours.

Fluorization at C2 is further described in PCT/IB99/02051, filed Dec. 28, 1999.

Compounds of the present invention wherein $R^4$ is other than ethyl may be prepared using starting materials obtained as described, e.g., in WO 98/01546, published Jan. 15, 1998; WO 98/01571, published Jan. 15, 1998; WO 00/0500, published Jan. 6, 2000; and WO 00/00618, published Jan. 6, 2000.

The compounds of the present invention may have asymmetric carbon atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The present invention includes all isotopically labelled forms of the compounds of formula I, and pharmaceutically acceptable salts and prodrugs thereof. Such isotopically labelled compounds are useful as research or diagnostic tools. The isotopically-labelled compounds and pharmaceutically acceptable salts thereof are identical to those of formula I but for the fact that one or more atoms are replaced by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Certain compounds of the present invention, such as those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Substitution with heavier isotopes such as deuterium, i.e., $^2$H, can afford certain therapeutic advantages resulting from greater metabolic stability, for example, increased in vivo half-life or reduced dosage requirements, and hence may be preferred in some circumstances. Isotopically labelled compounds of formula I of this invention and prodrugs thereof can generally be prepared by carrying out the procedures disclosed in the Scheme(s) and/or in the Example(s) below and substituting a readily available isotopically labelled reagent for a non-isotopically labelled reagent.

The antibacterial and antiprotozoa activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests-Sixth Edition; Approved Standard,* published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica.*

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37°

C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a 3×10³ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula I, and the pharmaceutically acceptable salts, prodrugs, tautomers, and solvates thereof (hereinafter "the active compounds"), may be administered through oral, parenteral, topical, or rectal routes in the treatment of bacterial and protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the present invention. It is understood that the present invention is not limited to the details of the Examples.

EXAMPLE 1

2'-Acetoxy-2-alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-methyl-aminocarbonyl[4-[4-(pyridin-3-yl)-1H-imidazol-1-yl]butyl]imino]]-erythromycin

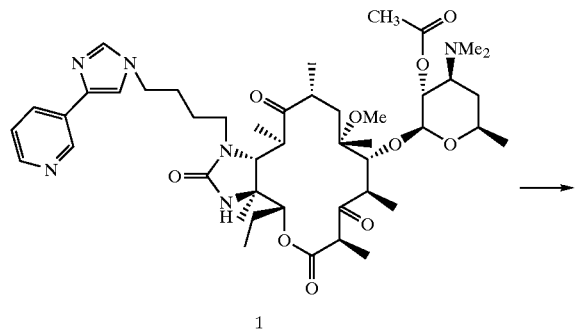

1

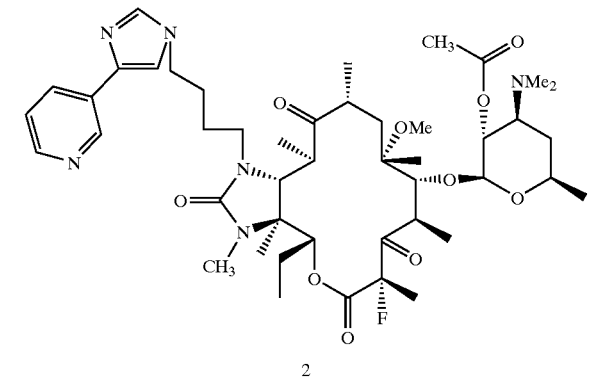

2

To a solution of 1 (18 mg, 0.021 mmol) in 1.5 mL of DMF was added at −78° C. a solution of KHMDS (42 μL of 0.5M solution in toluene, 0.021 mmol). After 15 minutes of stirring at −78° C., a solution of Selectfluor™ (8.2 mg, 0.023 mmol) in 500 μL of DMF was added dropwise. After 10 minutes of stirring at −78° C., fresh KHMS (50 μL, 0.025 mmol) was added. Methyliodide (15 μL 0.062 mmol) was then added dropwise after 15 minutes. The solution was stirred at this temperature for 15 minutes. The reaction was quenched by addition of a saturated NaHCO$_3$ solution and ethyl acetate. The organic layer was washed with a saturated NaHSO$_3$ solution and brine. Drying over Na$_2$SO$_4$ and removal of the solvent gave 18 mg of crude product, which was chromatographed on silica gel (10% CH$_3$OH—CH$_2$Cl$_2$) to give 12 mg (64%) of the title compound 2; MS m/e 885 (M+1).

EXAMPLE 2

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-methyl-aminocarbonyl[4-[4-(pyridin-3-yl)-1H-imidazol-1-yl]butyl]imino]]-erythromycin

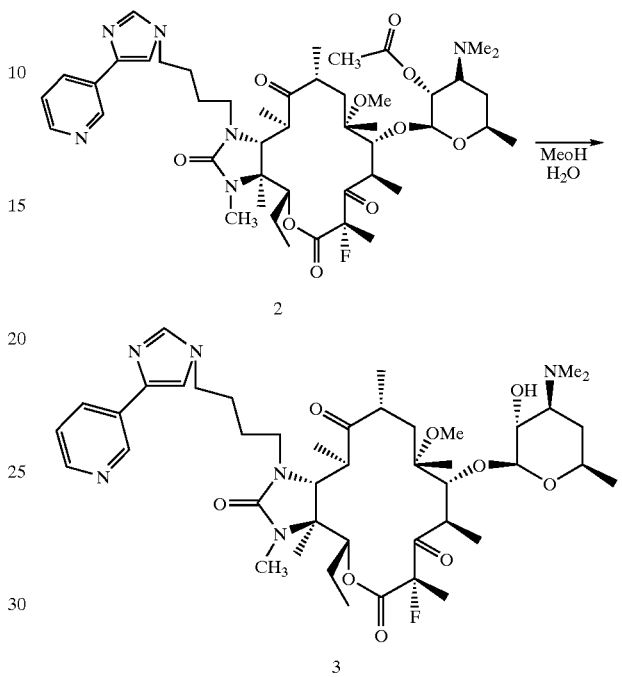

Compound 2 was dissolved in 1 mL of MeOH and 2 drops of water was added. The solution was stirred overnight at room temperature. Evaporation of the solvent gave 12 mg of id the title compound 3; MS 843 (M+1).

EXAMPLE 3

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-methyl-aminocarbonyl[4-[4-(pyridin-3-yl)-1H-imidazol-1-yl]butyl]imino]]-erythromycin Using the methods of Examples 1 and 2, a compound corresponding to 3 was prepared wherein R$^2$, as that variable is defined above for the compound of formula I, is CH$_2$CH$_3$; MS m/e 857(M+1)

EXAMPLE 4

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-methyl-aminocarbonyl[4-[4-(pyridin-3-yl)-1H-imidazol-1-yl]butyl]imino]]-erythromycin Using the methods of Examples 1 and 2, a compound corresponding to 3 was prepared wherein R$^2$, as that variable is defined above for the compound of formula I, is CH$_2$CH=CH$_2$; MS m/e 869 (M+1).

EXAMPLE 5

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-trans-2-butenyl-aminocarbonyl[4-[4-(pyridin-3-yl)-1H-imidazol-1-yl]butyl]imino]]-erythromycin Using the methods of Examples 1 and 2, a compound corresponding to 3 was prepared wherein R$^2$, as that variable is defined above for the compound of formula I, is trans-CH$_2$CH=CHCH$_3$; MS m/e 883 (M+1).

EXAMPLE 6

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-trans-2-pentenyl-aminocarbonyl[4-[4-(pyridin-3-yl)-1H-imidazol-1-yl]butyl]imino]]-erythromycin Using the methods of Examples 1 and 2, a compound corresponding to 3 was prepared wherein R$^2$, as that variable is defined above for the compound of formula I, is trans-CH$_2$CH=CHCH$_2$CH$_3$; MS m/e 897 (M+1).

EXAMPLE 7

2-Alpha-fluoro-11,12-dideoxy-3-de[(2,6-dideoxy-3-C-methyl-3-O-methyl-alpha-L-ribohexopyranosyl)oxy]-6-O-methyl-3-oxo-12,11-[[12-N-methyl-aminocarbonyl[4-[4-(pyridin-3-yl)-1H-imidazol-1-yl]butyl]imino]]-erythromycin Using the methods of Examples 1 and 2, a compound corresponding to 3 was prepared wherein R$^2$, as that variable is defined above for the compound of formula I, is trans, trans-CH$_2$—CH=C(CH$_3$)CH$_2$CH$_2$CH=(CH$_3$)CH$_3$; MS m/e 965 (M+1).

What is claimed is:

1. A compound of the formula

I or a pharmaceutically acceptable salt, prodrug, or solvate thereof, wherein:

X is Cl, Br, I, or F;

Y is =O or =NOR$^5$,

R$^1$ is (4- to 10-membered heterocyclic) C$_1$–C$_6$ alkyl, wherein the heterocyclic is substituted by 4- to 10-membered heterocyclic, R$^2$ is C$_1$–C$_{10}$ alkyl or C$_2$–C$_{10}$ alkenyl, R$^3$ is C$_1$–C$_6$ alkyl, R$^4$ is ethyl, R$^5$ is C$_1$–C$_6$ alkyl, and R$^6$ is H.

2. A compound of claim 1 of the formula

Ia or a pharmaceutically acceptable salt thereof wherein:

Y is =O or =NOR$^5$;

R$^2$ is C$_1$–C$_{10}$ alkyl or C$_2$–C$_{10}$ alkenyl; and

R$^6$ is H, —C(O)C$_1$–C$_6$ alkyl, benzyl, benzyloxycarbonyl, or (C$_1$–C$_6$ alkyl)$_3$ silyl.

3. The compound of claim 2 wherein Y is =O and R$^6$ H.

4. The compound of claim 2 wherein Y is =NOR$^5$ and R$^6$ is H.

5. The compound of claim 3 wherein R$^2$ is CH$_3$, CH$_2$CH$_3$, CH$_2$CH=CH$_2$, trans-CH$_2$CH=CHCH$_3$, trans-CH$_2$CH=CHCH$_2$CH$_3$, or trans-CH$_2$-CH=C(CH$_3$)CH$_2$CH$_2$CH=(CH$_3$)CH$_3$.

6. A method of preparing a compound of formula I

I or a pharmaceutically acceptable salt, prodrug, or solvate thereof, wherein:

X is Cl, Br, I, or F;

Y is =O, or =NOR$^5$; or Y means both —H and —OR$^5$; or both —H and —NR$^5$R$^{10}$;

R$^1$, R$^2$, and R$^3$ are independently selected from the group consisting of H, C$_1$–C$_{10}$ alkyl, C$_2$–C$_{10}$ alkenyl, C$_2$–C$_{10}$ alkynyl, (4- to 10-membered heterocyclic) C$_1$–C$_6$ alkyl, (4- to 10-membered heterocyclic) C$_2$–C$_6$ alkenyl, (4- to 10-membered heterocyclic) C$_2$–C$_6$ alkynyl, (C$_6$–C$_{10}$ aryl) C$_1$–C$_6$ alkyl, (C$_6$–C$_{10}$ aryl) C$_2$–C$_6$ alkenyl, and (C$_6$–C$_{10}$ aryl) C$_2$–C$_6$ alkynyl wherein said alkyl moieties of the foregoing groups are optionally substituted by halo or C$_1$–C$_6$ alkyl, and wherein said heterocyclic moieties are optionally substituted by 4- to 10-membered heterocyclic, (4- to 10-membered heterocyclic) C$_1$–C$_6$ alkyl, or (C$_6$–C$_{10}$ aryl) C$_1$–C$_6$ alkyl, and further wherein the aryl and heterocyclic moieties of each of the foregoing groups and optional substituents is optionally substituted by 1 to 4 R$^7$ groups;

$R^4$ is selected from the group consisting of H, $C_1$–$C_{10}$ alkyl, $C_2$–$C_6$ alkenyl, $C_2$–$C_6$ alkynyl, ($C_1$–$C_6$ alkoxy) $C_1$–$C_6$ alkyl, ($C_1$–$C_6$ alkylthio) $C_1$–$C_6$ alkyl, ($C_5$–$C_8$ cycloalkyl) $C_2$–$C_5$ alpha branched alkyl, $C_3$–$C_8$ cycloalkyl, $C_5$–$C_8$ cycloalkenyl, 3 to 6 membered O or S containing heterocyclic group, or phenyl, wherein each $R^4$ group may be substituted with from 1 to 3 substituents independently selected from the group consisting of hydroxy, halo, ($C_6$–$C_{10}$ aryl) $C_2$–$C_6$ alkenyl, and $C_1$–$C_4$ alkyl;

$R^5$ and $R^{10}$ are independently selected from the group consisting of H, $C_1$–$C_6$ alkyl, $C_6$–$C_{10}$ aryl, 4- to 10-membered heterocyclic, (4- to 10-membered heterocyclic) $C_1$–$C_6$ alkyl and ($C_6$–$C_{10}$ aryl) $C_1$–$C_6$ alkyl, wherein said aryl and heterocyclic groups are optionally substituted by 1 to 4 $R^7$ groups;

$R^6$ is H, —C(O)$C_1$–$C_6$ alkyl, benzyl, benzyloxycarbonyl, or ($C_1$–$C_6$ alkyl)$_3$ silyl;

$R^7$ is independently selected from the group consisting of halo, cyano, nitro, trifluoromethyl, trifluoromethoxy, azido, —C(O)$R^8$, —C(O)O$R^8$, —OC(O)$R^8$, —$NR^8$C (O)$R^9$, —C(O)$NR^8R^9$, —$NR^8R^9$, hydroxy, $C_1$–$C_6$ alkyl, $C_2$–$C_6$ alkenyl, $C_2$–$C_6$ alkynyl, $C_6$–$C_{10}$ aryl, 4- to 10-membered heterocyclic, and $C_1$–$C_6$ alkoxy; and each $R^8$ and $R^9$ is independently selected from the group consisting of H, $C_1$–$C_6$ alkyl, $C_6$–$C_{10}$ aryl, and 4- to 10-membered heterocyclic;

which comprises deprotecting a compound of the formula

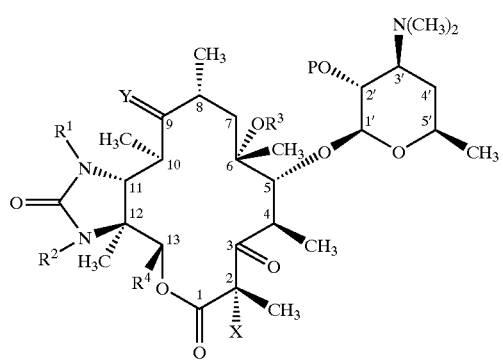

II wherein P is a protecting group.

7. The method of claim 6 further wherein the compound of formula II is prepared by treating a compound of the formula

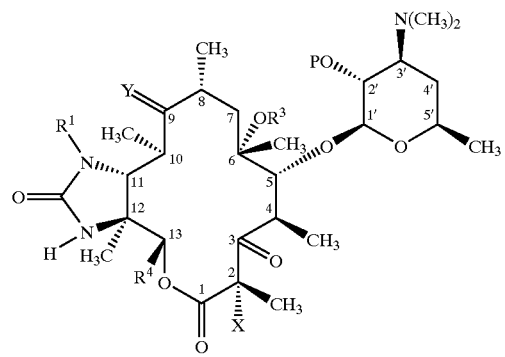

III with a strong base and a compound of formula $R^2$-L, where L is a leaving group, and wherein $R^2$ is selected from the group consisting of $C_1$–$C_{10}$ alkyl, $C_2$–$C_{10}$ alkenyl, $C_2$–$C_{10}$ alkynyl, (4- to 10-membered heterocyclic) $C_1$–$C_6$ alkyl, (4- to 10-membered heterocyclic) $C_2$–$C_6$ alkenyl, (4- to 10-membered heterocyclic) $C_2$–$C_6$ alkynyl, ($C_6$–$C_{10}$ aryl) $C_1$–$C_6$ alkyl, ($C_6$–$C_{10}$ aryl) $C_2$–$C_6$ alkenyl, and ($C_6$–$C_{10}$ aryl) $C_2$–$C_6$ alkynyl wherein said alkyl moieties of the foregoing groups are optionally substituted by halo or $C_1$–$C_6$ alkyl, and wherein said heterocyclic moieties are optionally substituted by 4- to 10-membered heterocyclic, (4- to 10-membered heterocyclic) $C_1$–$C_6$ alkyl, or ($C_6$–$C_{10}$ aryl) $C_1$–$C_6$ alkyl, and further wherein the aryl and heterocyclic moieties of each of the foregoing groups and optional substituents is optionally substituted by 1 to 4 $R^7$ groups.

8. A pharmaceutical composition for the treatment of a bacterial infection or a protozoa infection in a mammal, fish, or bird which comprises a therapeutically effective amount of a compound of claim 1, or a pharmaceutically acceptable salt, prodrug, or solvate thereof, and a pharmaceutically acceptable carrier.

9. A method of treating a bacterial infection or a protozoa infection in a mammal, fish, or bird which comprises administering to said mammal, fish or bird a therapeutically effective amount of a compound of claim 1, or a pharmaceutically acceptable salt, prodrug, or solvate thereof.

* * * * *